US011015160B2

(12) United States Patent
Faldt et al.

(10) Patent No.: US 11,015,160 B2
(45) Date of Patent: May 25, 2021

(54) FILTER HOLDING DEVICE

(71) Applicant: Cytiva Sweden AB, Uppsala (SE)

(72) Inventors: Eric Faldt, Uppsala (SE); Ralph Stankowski, Westborough, MA (US)

(73) Assignee: Cytiva Sweden AB, Uppsala (SE)

( * ) Notice: Subject to any disclaimer, the term of this patent is extended or adjusted under 35 U.S.C. 154(b) by 45 days.

(21) Appl. No.: 15/760,022

(22) PCT Filed: Sep. 12, 2016

(86) PCT No.: PCT/EP2016/071422
§ 371 (c)(1),
(2) Date: Mar. 14, 2018

(87) PCT Pub. No.: WO2017/055059
PCT Pub. Date: Apr. 6, 2017

(65) Prior Publication Data
US 2018/0346864 A1    Dec. 6, 2018

Related U.S. Application Data

(60) Provisional application No. 62/235,597, filed on Oct. 1, 2015.

(51) Int. Cl.
*C12M 1/00* (2006.01)
*C12M 3/06* (2006.01)

(52) U.S. Cl.
CPC ............ *C12M 29/04* (2013.01); *C12M 23/14* (2013.01); *C12M 23/26* (2013.01); *C12M 27/16* (2013.01)

(58) Field of Classification Search
CPC ...... C12M 29/04; C12M 23/14; C12M 23/26; C12M 27/16
See application file for complete search history.

(56) References Cited

U.S. PATENT DOCUMENTS

| 7,629,167 | B2 * | 12/2009 | Hodge | ................ B01F 13/0827 |
| | | | | 435/289.1 |
| 2003/0036192 | A1 | 2/2003 | Singh | |
| 2007/0070807 | A1 | 3/2007 | Bracht et al. | |
| 2009/0090244 | A1 * | 4/2009 | LeConey | .............. F25B 43/003 |
| | | | | 96/136 |

(Continued)

FOREIGN PATENT DOCUMENTS

| JP | 03007575 A | 1/1991 |
| WO | 2012/158108 A1 | 11/2012 |
| WO | 2015/034416 A1 | 3/2015 |

OTHER PUBLICATIONS

PCT International Search Report for PCT Application No. PCT/EP2016/071422 dated Nov. 29, 2016 (11 pages).

(Continued)

*Primary Examiner* — William H. Beisner
*Assistant Examiner* — Danielle B Henkel
(74) *Attorney, Agent, or Firm* — Eversheds Sutherland (US) LLP

(57) ABSTRACT

A filter holding device (1; 41; 75; 81) arranged for providing at least one filter (7; 43a, 43b; 85) inside a flexible bag (3; 71), said filter holding device comprising attaching means (19a-d, 21a-d; 79; 83) for attaching the filter holding device to an inner surface of the flexible bag such that the at least one filter held by the filter holding device is provided at a distance from the inner surface of the flexible bag.

12 Claims, 6 Drawing Sheets

(56) References Cited

U.S. PATENT DOCUMENTS

| | | |
|---|---|---|
| 2012/0238011 A1 | 9/2012 | Tuohey et al. |
| 2013/0059383 A1 | 3/2013 | Dijkhuizen Borgart et al. |
| 2013/0081995 A1 | 4/2013 | Larsen et al. |
| 2014/0011270 A1* | 1/2014 | Chotteau ................ C12M 23/14 435/326 |
| 2014/0193883 A1* | 7/2014 | Eriksson ................ C12M 37/02 435/243 |
| 2014/0287512 A1* | 9/2014 | Kaisermayer .......... C12M 23/14 435/456 |

OTHER PUBLICATIONS

Japanese Office Action for JP Application No. 2018-516819 dated Jun. 15, 2020 (10 pages).

* cited by examiner

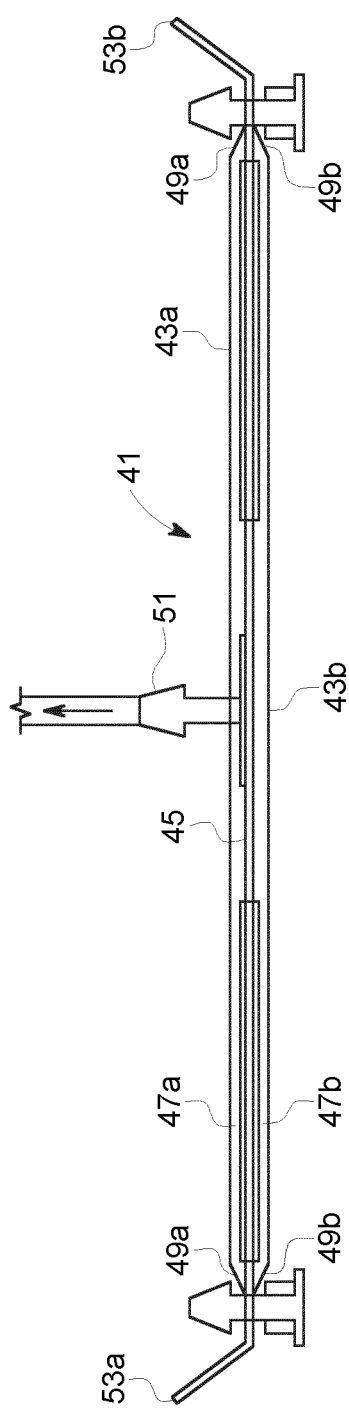

FILTER HOLDING DEVICE

CROSS REFERENCE TO RELATED APPLICATIONS

This application claims the priority benefit of PCT/EP2016/071422 filed Sep. 12, 2016 which claims priority benefit of U.S. Provisional Application No. 62/235,597 filed Oct. 1, 2015. The entire contents of which are hereby incorporated by reference herein.

TECHNICAL FIELD OF THE INVENTION

The present invention relates to a filter holding device arranged for providing at least one filter inside a flexible bag.

BACKGROUND OF THE INVENTION

The bio-processing industry has traditionally used stainless steel systems and piping in manufacturing processes for fermentation and cell cultivation. These devices are designed to be steam sterilized and reused. Cleaning and sterilization are however costly labour-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last ten years that of using plastic, single-use disposable bags and tubing, to replace the usual stainless steel tanks.

In particular bioreactors, traditionally made of stainless steel, have been replaced in many applications by disposable bags which are rocked to provide the necessary aeration and mixing necessary for cell culture. These single-use bags are typically provided as sterile units and eliminate the costly and time-consuming steps of cleaning and resterilization. The bags are designed to maintain a sterile environment during operation thereby minimizing the risk of contamination.

One of the successful disposable bioreactor systems uses a rocking table on which a bioreactor bag is placed. The bioreactor bag is partially filled with liquid nutrient media and the desired cells. The table rocks the bag providing constant movement of the cells in the bag and also efficient gas exchange from the turbulent air-liquid surface. The bag, typically, has at least one gas supply tube for the introduction of air, carbon dioxide, nitrogen or oxygen, and at least one exhaust gas tube to allow for the removal of respired gases. Nutrients can be added through other tubes.

During cultivation, the cells produce waste e.g. metabolites, ammonium ions and lactate, which have an inhibitory effect on cells. This effect becomes an issue particularly in cultivation at high cell densities, which are required for cost-effective production of biopharmaceuticals such as therapeutic proteins or virus antigens. One way to reduce the concentrations of inhibitory metabolites is to use perfusion cultivation where culture medium is bled off by hydraulic flow through a filter which retains the cells but lets the metabolites and proteins pass through the filter. Expressed proteins can then be recovered from the filtrate and fresh culture medium is continuously supplied to the bioreactor to compensate for the lost liquid. Perfusion filters can typically be installed in the interior of a bioreactor (or outside).

One way to provide a perfusion filter to a disposable bioreactor is to provide the perfusion filter to a device comprising a screen and having a connector for attaching a tube for retrieving filtrate, often waste, and just let the device with a filter and screen float within the bioreactor.

However, in a rocking bioreactor there are some drawbacks related to this. One problem is that the filter membranes which often are fragile, can get damaged by the screen when the screen and filter is forced into the bioreactor walls by the rocking motion. Another problem is related to the clogging and fouling of the filter.

Another way to provide a perfusion filter has been described in U.S. Pat. No. 9,017,997. Here it is described that the perfusion filter is attached to the bottom of the bioreactor bag. A problem with this is that a filter attached to the bottom of a bag probably will get clogged and fouled easily.

SUMMARY

An object of the invention is to provide a filter holding device for flexible bags.

A further object of the invention is to provide an improved perfusion filter system for a flexible bag.

This is achieved in a filter holding device arranged for providing at least one filter inside a flexible bag, said filter holding device comprising attaching means for attaching the filter holding device to an inner surface of the flexible bag such that the at least one filter held by the filter holding device is provided at a distance from the inner surface of the flexible bag.

Another object of the invention is to provide a bioreactor comprising a perfusion filter. This is achieved in a bioreactor comprising a filter holding device as described above, wherein said filter holding device is attached by its attaching means to an inner surface of the flexible bag such that the at least one filter held by the filter holding device is provided at a distance from the inner surface of the flexible bag.

Another object of the invention is to provide a method for providing a filter to a flexible bag.

This is achieved in a method comprising the steps of:
  providing at least one filter to a filter holding device as described above;
  attaching the filter holding device to an inner surface of the flexible bag such that the at least one filter held by the filter holding device is provided at a distance from the inner surface of the flexible bag;
  attaching a tube to a port provided in the filter holding device for retrieving filtrate.

Hereby the filter is provided at a distance from the inner surface of the flexible bag and a flow of the liquid provided in the flexible bag will be allowed between the filter and the flexible bag. Hereby a crossflow filtration effect is achieved, also called TFF and the filter can be used for a longer time because there are less problems with clogging and fouling of the filter.

In one embodiment of the invention the filter holding device comprises two flow deflector areas provided on opposite sides of the filter holding device, said flow deflector areas being angled in relation to the rest of the filter holding device such that they are pointing away from the surface of the flexible bag to which the filter holding device is attached when the filter holding device is provided in a flexible bag. Hereby the flow between the filter and the inner surface of the flexible bag will be increased.

Further embodiments are described in the dependent claims.

BRIEF DESCRIPTION OF THE D WINGS

FIG. 3b shows schematically a bottom view of the filter holding device shown in FIG. 3a.

FIG. 4 shows schematically a filter holding device according to another embodiment of the invention where two filters/membranes are attached to the same filter holding device.

FIG. 5b shows schematically a top view of the flexible bag shown in FIG. 5a.

DETAILED DESCRIPTION OF THE EMBODIMENTS

Figure 1:
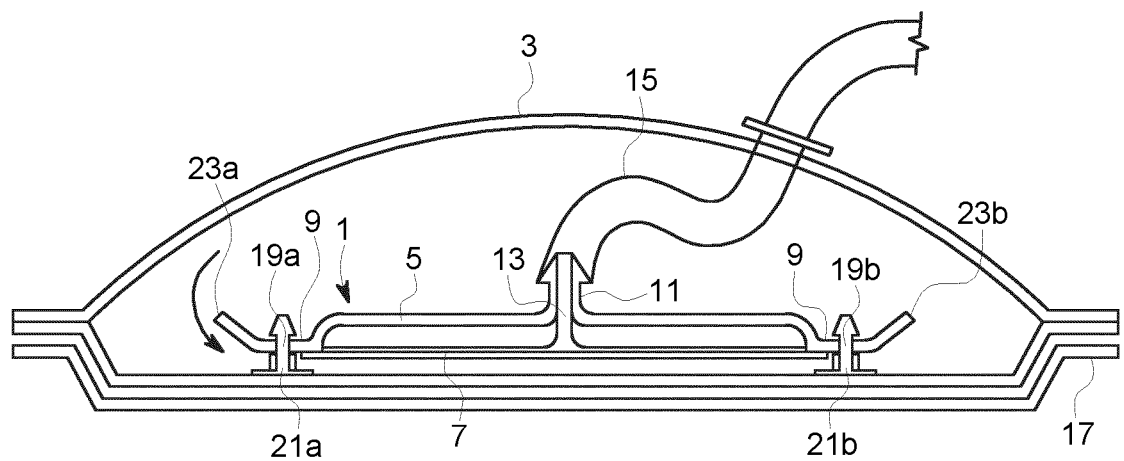
FIG. 1 shows schematically a cross section side view of a filter holding device according to one embodiment of the invention provided in a flexible bag.

FIG. 1 shows schematically a cross section side view of a filter holding device 1 according to one embodiment of the invention. The filter holding device 1 is provided in a flexible bag 3.

The filter holding device 1 is suitably a flat or somewhat curved plate. The filter holding device 1 comprises some kind of distancing means on one side of a middle part 5 of the filter holding device. This distancing means could be for example ribs or a screen or some other kind of structure. The distancing means is provided on the side of the filter holding device to which a filter 7 should be attached. In this description the word filter is used but it could also be a membrane or a bioprocessing separation device used to retain or refrain. A distancing means in the form of ribs are further shown and described in relation to FIG. 3b. The filter holding device 1 comprises further a filter sealing area 9 provided around the distancing means. The filter sealing area 9 is arranged to be sealed to a periphery of the filter 7 to be held by the filter holding device. The filter will then be covering the distancing means when it has been sealed to the filter sealing area 9 of the filter holding device. In one embodiment the filter can also be sealed to one or more areas of the distancing means in order to prevent the filter from slacking. Furthermore, the filter holding device comprises a port 11 arranged around an opening 13 in the filter holding device 1, which opening connects fluidically with the spaces between the ribs. Said port 11 is arranged to be connected to a tube 15 for retrieving filtrate, usually waste. The port 11 and opening 13 are in one embodiment of the invention provided in the middle of the filter holding device 1 and centered inside the filter sealing area 9. However, the port and opening can also be provided in another position but they still need to be provided within the filter sealing area 9.

The flexible bag is shown here placed in a rocker tray 17. Attaching means are provided to the filter holding device for attaching the filter holding device to an inner surface of the flexible bag such that the at least one filter held by the filter holding device is provided at a distance from the inner surface of the flexible bag. In this embodiment of the invention the attaching means are provided as four openings 19a-d (only 19a and 19b can be seen) in the filter holding device and four stand-offs 21a-d to be received in the openings. Each one of the stand-offs 21a-d is attached one to each opening 19a-d in the filter holding device in a suitable way for example by heat sealing or my mechanical retention. The stand-offs 21a-d are then attached to the flexible bag inner surface for example by heat sealing or mechanical retention. In this embodiment the stand-offs 21a-d are shown to be attached to the bottom wall of the flexible bag 3 but they could as well be attached to another wall as will be shown in relation to FIG. 5. Another possibility would also be that the stand-offs are molded together with the filter holding device. The number of openings and stand-offs and their positions could be varied. The height of the attaching means which in this shown embodiment are the stand-offs, should be adapted for assuring that there will be a suitable distance between the filter and the bag inner surface for letting fluid flow between the filter and the bag surface and thereby create a crossflow effect over the filter, also called tangential flow. This tangential flow or crossflow over the filter will prevent fouling and clogging and will increase the life time of the filter. In another embodiment the attaching means is in the form of sealing two opposite sides of the filter holding device to the inner surface of the flexible bag. In order to provide a passage or channel for the fluid to pass between the filter and the bag surface the filter holding device needs to be bent or curved in some way. See further details in FIG. 6.

In the embodiment shown in FIG. 1 the filter holding device 1 further comprises two deflector areas 23a, 23b. These deflector areas 23a, 23b are provided on opposite sides of the filter holding device and outside the filter sealing area 9. The deflector areas 23a, 23b are angled in relation to the rest of the filter holding device and they are pointing away from the inner surface of the flexible bag to which the filter holding device is attached when the filter holding device is mounted to the flexible bag. The deflector areas 23a, 23b affects the fluid flow in the flexible bag. The rocking tray is moved in a specific pattern such that the fluid inside the flexible bag is moving back and forth in a wave like motion. The deflector areas 23a, 23b will direct and force more fluid to pass between the filter and the bag surface to which the filter holding device is attached. Thereby a crossflow effect over the filter is created which will reduce clogging and fouling.

Figure 2:
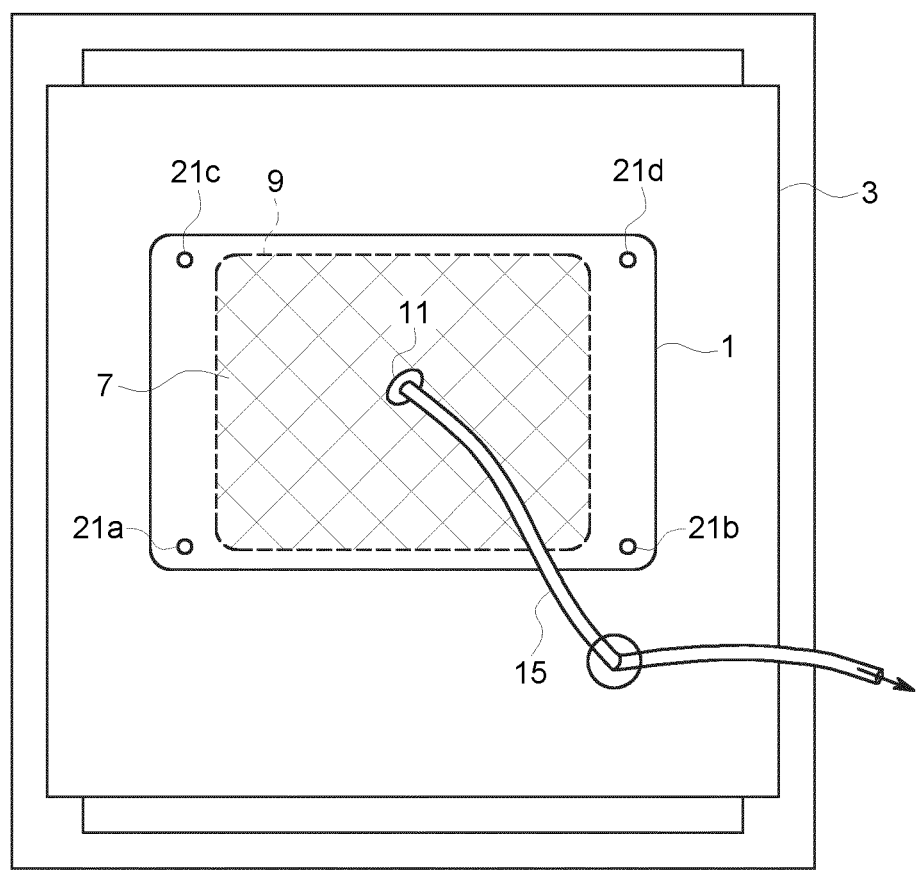
FIG. 2 shows schematically a top view of the flexible bag with a filter holding device shown in FIG. 1.

FIG. 2 shows schematically a top view of the flexible bag 3 with a filter holding device 1 shown in FIG. 1. Here it can be seen that in this embodiment there are provided four stand-offs 21a-d, one in each corner of the filter holding device 1.

Figure 3A:
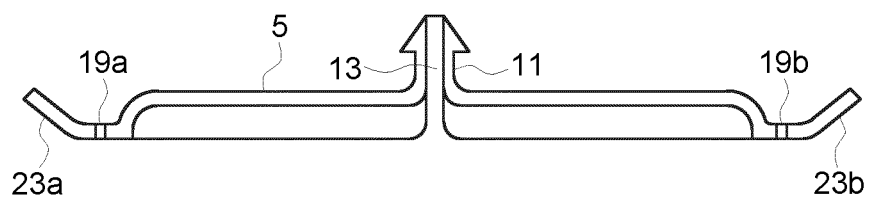
FIG. 3a shows schematically a filter holding device according to one embodiment of the invention in cross section side view.

FIG. 3a shows schematically the filter holding device 1 shown in FIGS. 1 and 2 in cross section side view.

Figure 3B:
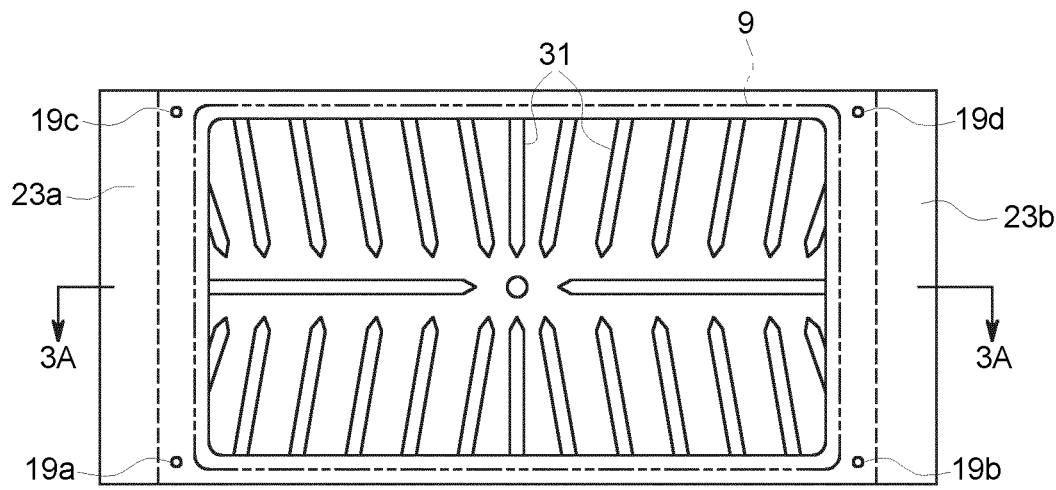

FIG. 3b shows schematically a bottom view of the filter holding device 1 shown in FIG. 3a. In this view the filter sealing area 9 can be seen to enclose the distancing means, here in the form of ribs 31. All the ribs are given the same numbers. The configuration and number of the ribs could vary. The function of the ribs is to hold the filter and distance the filter from the other side of the filter holding device such that the fluid can be filtered through the filter and drawn out through the opening 13 and port 11.

FIG. 4 shows schematically a filter holding device 41 according to another embodiment of the invention where two filters, a first filter 43a and a second filter 43b are attached to the same filter holding device 41. In this embodiment a middle part 45 of the filter holding device comprises a first distancing means, for example a first set of ribs 47a on one side and a second distancing means, for example a second set of ribs 47b on the other side instead of only ribs on one side as in the previously described embodiment. In this embodiment there are also provided two filter sealing areas, a first filter sealing area 49a and a second filter sealing area 49b, one on each side of the filter holding plate. The first filter sealing area 49a surrounds the first distancing means (in this embodiment the first set of ribs 47a) and the second filter sealing area 49b surrounds the second distancing means (in this embodiment the second set of ribs 47b). A port 51 is provided to the center or close to the center of the middle part 45. Said port 51 connecting the openings between the ribs to an outlet for the filtrate. Furthermore, as in the previously described embodiment there are provided one deflector area 53a, 53b in each end of the filter holding device 41. These deflector areas 53a, 53b are as in the previously described embodiment angled in relation to the rest of the filter holding device and are when the filter holding device is mounted to the flexible bag pointing away from the bottom surface of the bag (or from the inner surface of the bag to which the filter holding device is attached, not necessarily the bottom surface). Attaching means in the form of openings and stand-offs are provided in the same way as previously described for attaching the filter holding device to the flexible bag.

These filter holding devices, both as shown in FIGS. 1-3 and in FIG. 4 could be stacked onto each other if more filters are to be provided in the flexible bag.

Figure 5A:
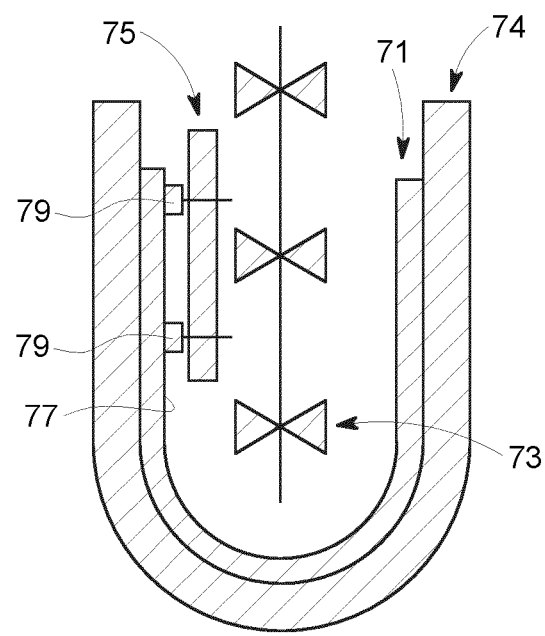
FIG. 5a shows schematically a cross section side view of another type of a flexible bag comprising an impeller. A filter holding device according to one embodiment of the invention is attached to a side wall of the flexible bag.

FIG. 5a shows schematically a cross section side view of another type of a flexible bag 71 comprising at least one impeller 73. This type of flexible bag is thus not provided on a rocking tray. Instead the content in the flexible bag is mixed by one or more impellers 73. The flexible bag 71 is normally provided in a rigid tank 74. A filter holding device 75 according to one embodiment of the invention is attached to an inner surface of a side wall 77 of the flexible bag 71. The filter holding device 75 comprises attaching means 79 here in the form of stand-offs. The attaching means 79 are attached to the inner surface of the side wall 77 of the flexible bag 71 as described above for the previous embodiments. As for the previously described embodiments the at least one filter held by the filter holding device 75 will hereby be provided at a distance from the inner surface of the side wall 77 of the flexible bag 71. Hereby a liquid provided in the flexible bag 71 can flow between the filter holding device 75 and the inner surface of the side wall 77 of the flexible bag 71 to which it is attached. Hereby a crossflow effect or tangential flow effect over the filter is achieved as discussed above.

Figure 5B:
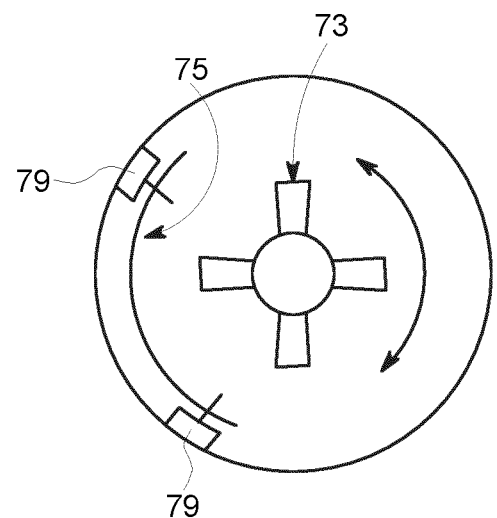

FIG. 5b shows schematically a top view of the flexible bag 71 shown in FIG. 5a. Here it can be seen that the filter holding device 75 according to this invention can be curved in order to follow the inner surface of the side wall 77 of the flexible bag 71.

Figure 6:
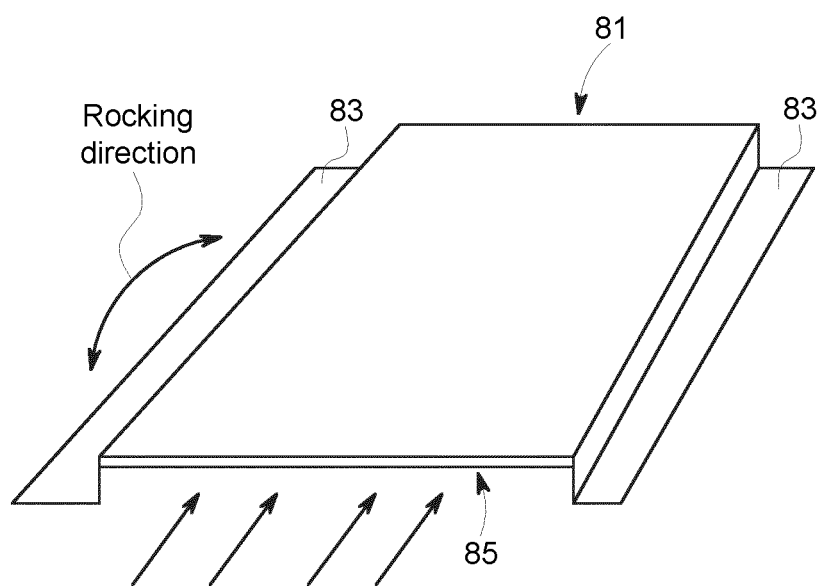
FIG. 6 shows schematically an alternative way to attach a filter holding device to an inner surface of a flexible bag.

FIG. 6 shows schematically an alternative way to attach a filter holding device 81 to an inner surface of a flexible bag. Attaching means 83 of the filter holding device 81 are provided as parts of two opposite sides of the filter holding device 81. Two opposite sides of the filter holding device are hereby attached to the inner surface of the flexible bag and the filter holding device is formed between these two opposite sides such that the filter holding device and thus an attached filter 85 is provided at a distance from the inner surface of the flexible bag. Hereby a fluid flow is allowed between the filter and the inner surface of the flexible bag in one direction, suitably the rocking direction in the embodiment where the flexible bag is provided in a rocking tray.

When a filter is to be provided in a flexible bag the following steps are performed according to the invention:

S1: Providing at least one filter to a filter holding device as described above. The filter can be sealed to the filter holding device.

S3: Attaching the filter holding device to an inner surface of the flexible bag such that the at least one filter held by the filter holding device is provided at a distance from the inner surface of the flexible bag. The filter holding device can be attached by sealing attaching means such as stand-offs provided to the filter holding device to the flexible bag. The stand-offs can be attached to a bottom wall of the flexible bag or another wall as also described above.

S5: Attaching a tube to a port provided in the filter holding device. Through this tube filtrate can be retrieved and taken out from the flexible bag.

The invention claimed is:

1. A filter holding device arranged for providing at least one filter inside a flexible bag, said filter holding device comprising attaching means for attaching the filter holding device to an inner surface of the flexible bag such that the at least one filter held by the filter holding device is provided within an interior of the flexible bag at a distance from the inner surface of the flexible bag,
   wherein the filter holding device comprises a plate,
   wherein the attaching means comprise stand-offs within an interior of the flexible bag,
   wherein the attaching means further comprises openings defined in the plate of the filter holding device for receiving the stand-offs, and
   wherein the plate is distinct from the filter.

2. A filter holding device according to claim 1, where the attaching means are attaching the filter holding device to the inner surface of the flexible bag in a way such that a liquid provided in the flexible bag can flow between the filter holding device and the inner surface to which it is attached.

3. A filter holding device according to claim 1, comprising at least two flow deflector areas provided on opposite sides of the filter holding device, said flow deflector areas being angled in relation to the rest of the filter holding device such that they are pointing away from the surface of the flexible bag to which the filter holding device is attached when the filter holding device is provided in a flexible bag.

4. A filter holding device according to claim 1, wherein
   a distancing means is provided on at least one side of the filter holding device to which side the at least one filter should be attached;
   a filter sealing area surrounding the distancing means and arranged to be sealed to a periphery of a filter to be held by the filter holding device, the filter will then be covering the distancing means;
   a port arranged around an opening in the filter holding device, said port being arranged to be connected to a tube for retrieving filtrate.

5. A filter holding device according to claim 1, wherein the stand-offs are attached to the inner wall of the flexible bag.

6. A filter holding device according to claim 4, wherein the openings or stand-offs are provided outside the filter sealing area.

7. A filter holding device according to claim 1, comprising:
   a first distancing means provided on one side of the filter holding device and a second distancing means provided on another side of the filter holding device,
   a first filter sealing area surrounding the first distancing means arranged to be sealed to a periphery of a first filter to be held by the filter holding device, the first filter will then be covering the first distancing means;

a second filter sealing area surrounding the second distancing means arranged to be sealed to a periphery of a second filter to be held by the filter holding device, the second filter will then be covering the second distancing means.

8. A flexible bag comprising a filter holding device according to claim 1, wherein said filter holding device is attached by its attaching means to the inner surface of the flexible bag such that the at least one filter held by the filter holding device is provided at a distance from the inner surface of the flexible bag.

9. A method for providing a filter in a flexible bag, said method comprising the steps of:
   providing at least one filter to the filter holding device according to claim 1;
   attaching the filter holding device to the inner surface of the flexible bag such that the at least one filter held by the filter holding device is provided at a distance from the inner surface of the flexible bag; and
   attaching a tube to a port provided in the filter holding device for retrieving filtrate.

10. A bioreactor comprising the flexible bag according to claim 8.

11. The bioreactor of claim 10, adapted for agitation by rocking motion, wherein the flexible bag is placed in a rocker tray.

12. The bioreactor of claim 10, adapted for agitation by an impeller, wherein the flexible bag comprises at least one impeller.

\* \* \* \* \*